(12) United States Patent
Kauffman et al.

(10) Patent No.: US 7,494,952 B2
(45) Date of Patent: Feb. 24, 2009

(54) PROCESS OF MAKING MIXED METAL OXIDE CATALYSTS FOR THE PRODUCTION OF UNSATURATED ALDEHYDES FROM OLEFINS

(75) Inventors: James W. Kauffman, Katy, TX (US); Angela McGuffey, Sugar Land, TX (US)

(73) Assignee: Saudi Basic Industries Corporation, Riyadh (SA)

(*) Notice: Subject to any disclaimer, the term of this patent is extended or adjusted under 35 U.S.C. 154(b) by 560 days.

(21) Appl. No.: 11/333,096

(22) Filed: Jan. 17, 2006

(65) Prior Publication Data

US 2007/0167657 A1 Jul. 19, 2007

(51) Int. Cl.
*B01J 33/00* (2006.01)
*B01J 21/00* (2006.01)

(52) U.S. Cl. .............. 502/305; 502/240; 502/255; 502/263; 502/313; 568/477

(58) Field of Classification Search .......... 502/240, 502/255, 263, 305, 313; 568/477
See application file for complete search history.

(56) References Cited

U.S. PATENT DOCUMENTS

| 3,984,477 | A | 10/1976 | Kubo et al. |
| 4,151,117 | A | 4/1979 | Schlaefer |
| 4,166,808 | A | 9/1979 | Daumas et al. |
| 4,388,223 | A | 6/1983 | Ferlazzo et al. |
| 7,232,788 | B2* | 6/2007 | Liang et al. ............... 502/311 |
| 2005/0159621 | A1 | 7/2005 | Liang et al. |

* cited by examiner

*Primary Examiner*—Kamal A Saeed
(74) *Attorney, Agent, or Firm*—Jim Wheelington

(57) ABSTRACT

The present invention is for a process for making a catalyst for production of unsaturated aldehydes, such as methacrolein, by gas phase catalytic oxidation of olefins, such as isobutylene, said catalyst containing oxides of molybdenum, bismuth, iron, cesium, tungsten, cobalt, nickel, antimony, magnesium and zinc. The process is a synthesis of the catalyst with aging or digestion of the reaction slurry with little or no agitation. A catalyst precursor is formed from the water insoluble and water soluble components and is dried. The metal oxide catalyst is formed by calcination of the catalyst precursor.

34 Claims, No Drawings

PROCESS OF MAKING MIXED METAL OXIDE CATALYSTS FOR THE PRODUCTION OF UNSATURATED ALDEHYDES FROM OLEFINS

BACKGROUND OF THE INVENTION

1. Field of the Invention

This invention relates to a process of making a mixed metal oxide catalyst containing oxides of molybdenum, bismuth, iron, cesium, and other metals for the production of unsaturated aldehydes from olefins, such as methacrolein by gas phase catalytic oxidation of isobutylene in the presence of air or another gas containing molecular oxygen.

2. Description of the Prior Art

Typically, the catalyst for oxidation of isobutylene to methacrolein is a mixed metal oxide prepared by mixing compounds containing the desired elements in a solution or a suspension and drying the resulting concentrate. Thereafter, the dried product is calcined. The calcined product may be ground or formed to a mesh size suitable for use. The prepared catalyst can be prepared with a specific surface area. The catalysts may be supported on a suitable carrier, such as silica, silica-containing materials, silicon carbide, alumina and the like, in order to improve the physical properties of the catalysts. Many methods of making catalysts for use in the production of acrolein or methacrolein by catalytic vapor phase oxidation of propylene or isobutylene have been disclosed.

U.S. Pat. No. 4,388,223 discloses a catalyst for conversion of unsaturated hydrocarbons into unsaturated aldehydes and nitrites. Example 18 discloses a catalyst prepared by dissolving ammonium paramolybdate, 85 wt. % phosphoric acid and colloidal silica LUDOX AS containing 40% of $SiO_2$ and water, forming a mixture of fused nitrates and pouring it into the solution which is maintained at 80° C. under agitation. A precipitate forms and a 30% aqueous solution of $NH_4OH$ is gradually added to set the pH value to 5.5, followed by a heat treatment at 80° C. for 4 hours, while controlling the pH value to 5.5.

U.S. Pat. No. 4,166,808 discloses a catalyst of oxides of cobalt, molybdenum, bismuth and iron for oxidizing olefins to $\alpha,\beta$-unsaturated aldehydes. In Example 1, cobalt nitrate hydrate, iron nitrate hydrate and bismuth nitrate hydrate (with concentrated nitric acid for promoting the dissolution of the bismuth nitrate) were separately dissolved in water, the three nitrate solutions were mixed, ammonium heptamolybdate was dissolved in water, the nitrate solution was slowly added to the heptamolybdate solution with strong agitation to form a suspension which was further agitated at room temperature during 30 minutes. The mixture was heated to 80° C. in order to evaporate the water.

U.S. Pat. No. 4,151,117 discloses a supported catalyst of oxides of antimony, tin, tellurium, arsenic, bismuth or cadmium, iron or cobalt and molybdenum or tungsten for preparation of unsaturated acids, nitriles and aldehydes by oxidation. In Examples 1, 3, 5 and 7 agitation of the thick slurry formed by the catalyst components continues until the addition is complete and through raising the temperature to strip water off to form a thick paste.

U.S. Pat. No. 3,984,477 discloses a catalyst of molybdenum, bismuth and iron, nickel or cobalt. Separate solutions of ammonium molybdate and ethylenediamine-tetraacetic acid dissolved under heating in silica sol and of ferric nitrate, bismuth nitrate and potassium nitrate dissolved under heating in nitric acid-acidified silica sol were formed and mixed. The liquid mixture was heated and concentrated under agitation to form a slurry which was dried and heated to decompose the nitrates.

Prior art discloses different methods of making mixed metal oxide catalysts which contain molybdenum, bismuth, iron, cesium and other metals for the production of methacrolein. The advantages of a particular method of making or order of addition wherein the reaction slurry is aged or digested for a period of time with controlled agitation has not been disclosed.

SUMMARY OF THE INVENTION

The present invention is for a process of making a catalyst of the general formula:

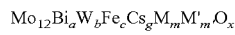

$$Mo_{12}Bi_aW_bFe_cCs_gM_mM'_{m'}O_x$$

wherein M is one or more of antimony, phosphorus, boron, sulfur, silicon, aluminum, titanium, tellurium, vanadium, zirconium and niobium and M' is one or more selected from cobalt, nickel, magnesium, zinc, potassium, rubidium, thallium, manganese, barium, chromium, cerium, tin, lead, cadmium and copper, a is in the range from 0.1 to 1.5, b is 0 to 9, c is in the range from 0.2 to 5.0, g is in the range from 0.1 to 1.5, m is in the range from 0 to 9, m' is from 0 to 9 and x is determined by the valences of the other components.

The process of making the catalyst is generally to mix the metal compounds of molybdenum, bismuth, iron, cesium, tungsten, M and M' in a reaction solution and precipitate solids to form reaction slurry, evaporating liquid to form a solid catalyst precursor which is calcined to form a mixed metal oxide catalyst. The metal compounds may be salts (e.g., nitrates, halides, ammonium, organic acid, inorganic acid), oxides, hydroxides, carbonates, oxyhalides, sulfates and other groups which may exchange with oxygen under high temperatures so that the metal compounds become metal oxides. It is preferable that the molybdenum compound and the tungsten compound are anunonium salts, that the bismuth compound, the ferric compound, the nickel compound, the cobalt compound, the magnesium compound, the zinc compound, the cesium compound, the potassium compound, the rubidium compound, the thallium compound, the manganese compound, the barium compound, the chromium compound, the boron compound, the sulfur compound, the silicon compound, the aluminum compound, the titanium compound, the cerium compound, the tellurium compound, the tin compound, the vanadium compound, the zirconium compound, the lead compound, the cadmium compound, the copper compound and the niobium compound are nitrates, oxides or acids and the antimony compound is an oxide.

The process of the present invention is a synthesis of the catalyst with a particular digestion or aging time of the reaction slurry with particular agitation.

This synthesis produces a catalyst with improved activity and selectivity of isobutylene oxidation to methacrolein.

DESCRIPTION OF EMBODIMENTS OF THE INVENTION

The present invention is for a process for making a catalyst for producing an unsaturated aldehyde, such as acrolein or methacrolein, by oxidation of an olefin, such as propylene or isobutylene. The exact chemical structure of the catalysts of this invention is not known. However, it is presumed that the catalyst is a homogeneous mixture of the oxides and/or complex oxides of all the components.

The catalyst is a mixed metal oxide of the formula:

$$Mo_{12}Bi_aW_bFe_cCs_gM_mM'_{m'}O_x$$

wherein M is one or more of antimony, phosphorus, boron, sulfur, silicon, aluminum, titanium, tellurium, vanadium, zirconium and niobium and M' is one or more selected from cobalt, nickel, magnesium, zinc, potassium, rubidium, thallium, manganese, barium, chromium, cerium, tin, lead, cadmium and copper, a is in the range from 0.1 to 1.5, b is 0 to 9, c is in the range from 0.2 to 5.0, g is in the range from 0.1 to 1.5, m is in the range from 0 to 9, m' is from 0 to 9 and x is determined by the valences of the other components.

One embodiment of the catalyst is of the formula:

$$Mo_{12}Bi_aW_bFe_cCo_dNi_eSb_fCs_gMg_hZn_iO_x$$

wherein a is 0.8 to 1.2, b is 0 to 2, c is 2 to 4 d is 0 to 4, e is 3 to 6, f is 0 to 2.0, g is 0.2 to 0.8, h is 0 to 1.5 and i is 0 to 2.0.

Another embodiment of the catalyst is of the formula:

$$Mo_{12}Bi_aW_bFe_cCo_dNi_eSb_fCs_gMg_hZn_iO_x$$

wherein a is 0.9 to 1.1, b is 0 to 1, c is 2.0 to 2.5, d is 1.0 to 2.0, e is 3.5 to 4.5, f is 0 to 1.0, g is 0.4 to 0.6, h is 0.25 to 0.75 and i is 0 to 1.

The process of making the catalyst is generally to form a solution of the metal compounds and precipitate solids at a temperature in the range of from 40° C. to 100° C. or 60° C. to 95° C. to form a slurry. Liquid is evaporated to leave a catalyst precursor which is calcined to form a mixed metal oxide catalyst. The metal compounds may be salts (e.g., nitrates, halides, ammonium, organic acid, inorganic acid), oxides, hydroxides, carbonates, oxyhalides, sulfates and other groups which may exchange with oxygen under high temperatures so that the metal compounds become metal oxides. It is more preferred that the molybdenum compound and the tungsten compound are ammonium salts, such as ammonium paramolybdate or ammonium molybdate and ammonium paratungstate or ammonium tungstate, respectively, that the bismuth, iron, cobalt, nickel, cesium, magnesium, zinc, phosphorus, potassium, rubidium, thallium, manganese, barium, chromium, boron, sulfur, silicon, aluminum, titanium, cerium, tellurium, tin, vanadium, zirconium, lead, cadmium, copper and niobium compounds are nitrates, oxides or acids and that the antimony compound is an oxide, such as antimony oxide or antimony trioxide. For bismuth, iron, cesium, cobalt, nickel, magnesium and zinc compounds, it is preferred that they are nitrates.

The present invention depends on particular process variables in the synthesis of the catalyst, specifically agitation of the reaction slurry and aging or digestion of the reaction slurry. Preferably, the reaction solution or slurry is agitated during and after additions of the components to obtain a uniform color, but there is little or no agitation during aging or digestion of the reaction slurry.

An example of making the catalyst of the claimed invention is to form a first solution of an ammonium salt of molybdenum, such as ammonium paramolybdate or ammonium molybdate, optionally, an ammonium salt of tungsten, such as ammonium paratungstate or ammonium tungstate, to form a second solution of a bismuth nitrate dissolved in an acid and to form a third solution of an iron nitrate, a cobalt nitrate, a nickel nitrate, a magnesium nitrate and a zinc nitrate in water to form a divalent metal nitrate solution. The bismuth nitrate (second) solution is added to the molybdenum (first) solution and a solid precipitate of the water insoluble metal components forms in the solution. The metal nitrate (third) solution of metal nitrates is added to form a reaction slurry. The bismuth nitrate (second) solution and the metal nitrate (third) solution may be combined and added together to the molybdenum (first) solution. Antimony oxide and cesium nitrate may be added to the reaction slurry as solids. The reaction slurry is agitated sufficiently to a uniform color. For the examples below, a magnetic stir bar was used in about a 500 mL round bottom flask and rotated at about 350 rpm to create a vortex to about the bottom of the slurry. The reaction slurry is then aged 5 to 10 hours, preferably about 5 to 6 hours, with little or no agitation. Liquid of the slurry is removed by evaporation to form a catalyst precursor from the solid precipitate and the water soluble components. The liquid may be evaporated at a temperature of is 50° C. to 125° C. The catalyst precursor may be further dried in air or an inert gas and in an oven or a spray dryer. The liquid may be removed and the catalyst precursor dried at the same time by spray drying or drying may be done separately. One example of separate drying is at a temperature of 100-150° C. for 2-5 hours in an oven in air.

The catalyst precursor is calcined to obtain a catalyst. One purpose of calcination of the catalyst precursor is to obtain an oxide of the metal components. The catalyst precursor may be calcined at a temperature of 200-600° C. for 1-12 hours. Calcination may be in two stages, one at a temperature of 150-400° C. for 1-5 hours and another at a temperature of 460-600° C. for 4-8 hours. For a two-stage calcination, preferably, the first is at a temperature of 290-310° C. for 2 hours and second at a temperature of 460-500° C. for 6 hours with an increase in temperature from the first stage to the second stage at 0.5 to 20° C./min, preferably 5 to 10° C./min. Drying and denitrification may occur in the first step. In the alternative, calcination is in one stage at a temperature of 450-500° C. for 1-4 hours with a temperature ramp of 0.5 to 20° C./min, preferably 5 to 10° C./min, from ambient temperature instead of an initial step or denitrification. Calcination may be done in a high temperature oven or kiln.

The X-ray diffraction pattern of the mixed metal oxide catalyst of the present invention is not substantially different from catalysts made by other processes. The catalyst compositions of the Examples above have a characteristic X-ray diffraction having diffraction peaks at the diffraction angles of 2θ, measured by using Cu Kα radiation, at about 9.6, 14.2, 23.0, 26.7 and 28.0 degrees. X-ray diffraction patterns of the catalysts of the Comparative Examples show the same diffraction peaks.

The catalyst may be processed by sieving, forming and other means known in the art to obtain catalyst particles of a certain size. Desired particle size and particle size distribution are related to the design of the reactor (size, shape, configuration, etc.), to the pressure drop intended for the process and to the process flow. For a two stage calcination, the catalyst may be sieved or formed after the first stage calcination and before the second stage calcination. In a commercial process the catalyst precursor may be sieved and formed after spray drying and before calcination.

The catalyst of the present invention may be used as an unsupported catalyst or a supported catalyst. The surface area of an unsupported catalyst is from 0.1 to 150 m²/g, preferably from 1 to 20 m²/g. If supported, the support should be an inert solid which is chemically unreactive with any of the active components of the catalyst and is preferably silica, alumina, niobia, titania, zirconia or mixtures thereof. The catalyst may be affixed to the support by methods known in the art, including incipient wetness, slurried reactions and spray drying. The catalyst is not limited by shape, size or particle distribution and may be formed as appropriate for the reaction vessel in the process. Examples are powder, granules, spheres, cylinders, saddles, etc.

The catalyst is used in the gas phase catalytic oxidation of a feedstock gas comprising an olefin; e.g., propylene or isobutylene; oxygen, water and an inert gas, such as nitrogen, to produce an unsaturated aldehyde, such as acrolein or methacrolein. Oxygen may be supplied in the pure form or in an oxygen containing gas, such as air or as an oxygen-diluent gas mixture. The diluent gas may be nitrogen, a hydrocarbon which is gaseous under the process conditions or carbon dioxide. The reaction temperature is preferably from 250-450° C., most preferably 370-410° C. The reactor may be a fixed bed or a fluidized bed reactor. Reaction pressure may be from 0 to 100 psig. Space velocity may be from 800 to 10,000 $hr^{-1}$.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

In this experiment there was no agitation during mixing of the reagent solutions and no agitation during the 6 hour digestion period. Three separate reagent solutions were prepared. In the first reagent solution 43.572 g of ammonium molybdate and 1.655 g of ammonium tungstate were dissolved in 87 g of water and agitated to completely dissolve the reagents at about 95° C. In the second solution, 9.978 g of bismuth nitrate were dissolved in a solution of 1.850 g concentrated nitric acid and 9.312 g of water. In the third solution 19.941 g $Fe(NO_3)_2$, 23.925 g $Ni(NO_3)_2$, 12.033 g $Co(NO_3)_2$, 2.638 g $Mg(NO_3)_2$, and 3.243 g $Zn(NO_3)_2$ were dissoved in 85.3 g of water.

The bismuth nitrate (second) solution and mixed metal nitrates (third) solution were combined and added to the ammonium molybdate (first) solution at about 95° C. over about 27 minutes forming a slurry. The slurry was not agitated during the addition of the bismuth nitrate and metal nitrate solutions.

After the metal nitrates were added, 2.42 g $CsNO_3$ and 2.114 g of $Sb_2O_3$ were added all at once to the above slurry without agitation.

The slurry was digested for 6 hours at about 95° C. After digestion the water was evaporated at about 60° C. to make a paste. The paste was dried at 100° C. overnight. The dried cake was sized to 3-5 mm particles and calcined at 485° C., for 2 hours with a 10° C./min ramp rate with an airflow of about 5 liters minute. The catalyst was sized to −20+30 mesh for reactor testing.

EXAMPLE 2

In this experiment there was minimum agitation during reagent addition and no agitation during the 6 hour digestion period. Three separate reagent solutions were prepared. In the first reagent solution 43.587 g of ammonium molybdate and 1.65 g of ammonium tungstate were dissolved in 87 g of water and agitated to completely dissolve the reagents. In the second solution, 9.972 g of bismuth nitrate were dissolved in a solution of 1.859 g concentrated nitric acid and 9.34 g of water. In the third solution 19.94 g $Fe(NO_3)_2$, 23.924 g $Ni(NO_3)_2$, 12.031 g $Co(NO_3)_2$, 2.638 g $Mg(NO_3)_2$, and 3.238 g $Zn(NO_3)_2$ were dissolved in 85.3 g of water.

The bismuth nitrate (second) solution and the mixed metal nitrates (third) solution were combined and added to the ammonium molybdate (first) solution at about 95° C. over 30 minutes forming a slurry. The slurry was agitated using a magnetic stir bar in a 500 mL flask at up to 350 rpm for the first 20 minutes of addition and not agitated for the last 10 minutes of the metal nitrate addition.

One hour after the metal nitrates were added, 2.42 g $CsNO_3$ and 2.116 g of $Sb_2O_3$ were added all at once to the above slurry and agitated for 1 minute using a magnetic stir bar at up to about 350 rpm.

The slurry was digested with no agitation for 6 hours at about 95° C. After digestion the water was evaporated at 50-75° C. to make a paste. The paste was dried at 120° C. for 3 hours. The dried cake was sized to 3-5 mm particles and calcined at 485° C., for 2 hours with a 10° C./min ramp rate and an airflow of about 5 liters per minute. The catalyst was sized to −20+30 mesh for reactor testing.

EXAMPLE 3

This example is similar to Example 2 except with relatively less agitation during metal nitrates addition and no agitation during the 6 hour digestion period. Three separate reagent solutions were prepared. In the first reagent solution 43.578 g of ammonium molybdate and 1.65 g of ammonium tungstate were dissolved in about 87 g of water and agitated to completely dissolve the reagents. In the second solution, 9.968 g of bismuth nitrate were dissolved in a solution of 1.83 g concentrated nitric acid and 9.3 g of water. In the third solution 19.942 g $Fe(NO_3)_2$, 23.912 g $Ni(NO_3)_2$, 12.036 g $Co(NO_3)_2$, 2.637 g $Mg(NO_3)_2$, and 3.237 g $Zn(NO_3)_2$ were dissolved in 85.8 g of water.

The bismuth nitrate (second) solution and the mixed metal nitrates (third) solution were combined and added to the ammonium molybdate (first) solution at about 95° C. over 50 minutes forming a slurry. The slurry was agitated periodically during the metal nitrate addition.

After the metal nitrates were added, 2.412 g $CsNO_3$ and 2.119 g of $Sb_2O_3$ were added all at once over 3.5 minutes to the above slurry and briefly agitated for several minutes until a uniform colored slurry was obtained.

The slurry was digested for 6 hours at about 95° C. without agitation. After digestion the water was evaporated at 50° C. to make a paste. The paste was dried at 120° C. for 2 hours. The dried cake was sized to 3-5 mm particles and calcined at 486° C., for 2 hours with a 10° C./min ramp rate and an airflow of about 5 liters per minute. The catalyst was sized to −20+30 mesh for reactor testing.

COMPARATIVE EXAMPLE 1

In this experiment there was high agitation during reagent addition and high agitation during the 2 hour digestion period. Three separate reagent solutions were prepared. In the first reagent solution 43.575 g of ammonium molybdate and 1.658 g of ammonium tungstate were dissolved in 87 g of water and agitated to completely dissolve the reagents. In the second solution, 9.975 g of bismuth nitrate were dissolved in a solution of 1.835 g concentrated nitric acid and 9.350 g of water. In the third solution 19.94 g $Fe(NO_3)_2$, 23.929 g $Ni(NO_3)_2$, 12.036 g $Co(NO_3)_2$, 2.637 g $Mg(NO_3)_2$, and 3.238 g $Zn(NO_3)_2$ were dissolved in 85.3 g of water.

The bismuth nitrate (second) solution and the mixed metal nitrates (third) solution were combined and added to the ammonium molybdate (first) solution at about 95° C. over about 30 minutes forming a slurry. A magnetic stir bar in a 500 mL flask was agitated at 350-450 rpm during addition of the metal nitrate solution After the metal nitrates were added, 2.42 g CsNO$_3$ and 2.119 g of Sb$_2$O$_3$ were added all at once to the above slurry and agitated using a magnetic stir bar at 350-450 rpm.

The slurry was digested for 2 hours at about 95° C. with agitation. After digestion the water was evaporated at about 50° C. to make a paste. The paste was dried at 120° C. for 3 hours. The dried cake was sized to 3-5 mm particles and calcined at 485° C., for 2 hours with a 10° C./min ramp rate and an airflow of about 5 liters per minute. The catalyst was sized to −20+30 mesh for reactor testing.

COMPARATIVE EXAMPLE 2

In this experiment there was high agitation during reagent addition and high agitation during the 10 hour digestion period. Three separate reagent solutions were prepared. In the first reagent solution 43.575 g of ammonium molybdate and 1.658 g of ammonium tungstate were dissolved in 87 g of water and agitating to completely dissolve the reagents. In the second solution, 9.975 g of bismuth nitrate were dissolved in a solution of 1.835 g concentrated nitric acid and 9.350 g of water. In the third solution 19.94 g Fe(NO$_3$)$_2$, 23.929 g Ni(NO$_3$)$_2$, 12.036 g Co(NO$_3$)$_2$, 2.637 g Mg(NO$_3$)$_2$, and 3.238 g Zn(NO$_3$)$_2$ were dissolved in 85.3 g of water.

The bismuth nitrate (second) solution and the mixed metal nitrates (third) solution were combined and added to the ammonium molybdate (first) solution at about 95° C. over about 30 minutes forming a slurry. A magnetic stir bar in a 500 mL flask was agitated at 350-450 rpm during addition of the metal nitrate solution.

After the metal nitrates were added, 2.42 g CsNO$_3$ and 2.119 g of Sb$_2$O$_3$ were added all at once to the above slurry and agitated using a magnetic stir bar at 350-450 rpm.

The slurry was digested for 10 hours at about 95° C. with agitation. After digestion the water was evaporated at about 50° C. to make a paste. The paste was dried at 120° C. for 3 hours. The dried cake was sized to 3-5 mm particles and calcined at 485° C, for 2 hours with a 10° C./min ramp rate and an airflow of about 5 liters per minute. The catalyst was sized to −20+30 mesh for reactor testing.

COMPARATIVE EXAMPLE 3

In this experiment there was moderate agitation during reagent addition and moderate agitation during the 6 hour digestion period. Three separate reagent solutions were prepared. In the first reagent solution 43.572 g of ammonium molybdate and 1.653 g of ammonium tungstate were dissolved in about 87 g of water and agitated to completely dissolve the reagents. In the second solution, 9.978 g of bismuth nitrate were dissolved in a solution of 1.832 g concentrated nitric acid and 9.304 g of water. In the third solution 19.942 g Fe(NO$_3$)$_2$, 23.926 g Ni(NO$_3$)$_2$, 12.029 g Co(NO$_3$)$_2$, 2.639 g Mg(NO$_3$)$_2$, and 3.239 g Zn(NO$_3$)$_2$ were dissolved in about 85 g of water.

The bismuth nitrate (second) solution and the mixed metal nitrates (third) solution were combined and added to the ammonium molybdate (first) solution at about 95° C. over 50 minutes forming a slurry. The slurry was agitated using a magnetic stir bar in a 500 mL flask at about 350 rpm during the metal nitrate addition.

After the metal nitrates were added, 2.413 g CsNO$_3$ and 2.118 g of Sb$_2$O$_3$ were added all over about 3 minutes to the above slurry and with continuous agitation.

The slurry was digested for 6 hours at about 95° C. with agitation. After digestion the water was evaporated at 50° C. to make a paste. The paste was dried at 120° C. for 2 hours. The dried cake was sized to 3-5 mm particles and calcined at 486° C., for 2 hours with a 10° C./min ramp rate and an airflow of about 5 liters per minute. The catalyst was sized to −20+30 mesh for reactor testing.

COMPARATIVE EXAMPLE 4

In this experiment there was high agitation during reagent addition and high agitation during the 5 hour digestion period. Three separate reagent solutions were prepared. The first reagent solution involved dissolving 43.575 g of ammonium molybdate and 1.658 g of ammonium tungstate in 87 g of water and agitating to completely dissolve the reagents. In the second solution, 9.975 g of bismuth nitrate was dissolved in a solution of 1.835 g concentrated nitric acid and 9.350 g of water. A third solution of 19.94 g Fe(NO$_3$)$_2$, 23.929 g Ni(NO$_3$)$_2$, 12.036 g Co(NO$_3$)$_2$, 2.637 g Mg(NO$_3$)$_2$, and 3.238 g Zn(NO$_3$)$_2$ were dissolved in 85.3 g of water.

The bismuth nitrate (second) solution and mixed metal nitrates (third) solution were combined and added to the ammonium molybdate (first) solution at about 95° C. over about 30 minutes forming a slurry. A magnetic stir bar in a 500 mL flask was agitated at 350-450 rpm during addition of the metal nitrate solution.

After the metal nitrates were added, 2.42 g CsNO$_3$ and 2.119 g of Sb$_2$O$_3$ were added all at once to the above slurry and agitated using a magnetic stir bar at 350-450 rpm.

The slurry was digested for 5 hours at about 95° C. with agitation. After digestion the water was evaporated at about 50° C. to make a paste. The paste was dried at 120° C. for 3 hours. The dried cake was sized to 3-5 mm particles and calcined at 485° C., for 2 hours with a 10° C./min ramp rate and an airflow of about 5 liters per minute. The catalyst was sized to −20+30 mesh for reactor testing.

For each of the catalysts from the Examples and Comparative Examples above, 1.5 cc of catalyst were mixed with quartz chips to make a total volume of 5 cc, which were placed into a downflow reactor having an internal diameter of 0.25 inches. A gas consisting of about 3.6% isobutylene, 8.6% oxygen, 28% water and the balance as nitrogen was passed over the catalyst bed in the reactor. The volumetric flow rates were about 50-250 sccm. The internal reactor temperature and pressure were maintained at 380° C. and about 0 psig. The gas hourly space velocity was about 2500 hr$^{-1}$. The concentrations of isobutylene, methacrolein and other byproducts were determined from on-line analysis by gas chromatography.

Catalyst activities are reported in Table relative to a standard for which 1.5 cc of catalyst at a flow rate of 250 sccm gave 98% conversion and 88% selectivity to methacrolein. This standard as shown in Comparative Example 2 is defined to have relative activity of 1.0 and relative selectivity of zero. If the catalyst showed an activity 30% higher than the standard catalyst, then this catalyst would have a relative selectivity of 1.3. If the catalyst showed a selectivity 1.0% higher than the standard catalyst at the same conversion, then this catalyst would have a relative selectivity of 1.0.

TABLE

| | Relative Activity | Relative Selectivity |
| --- | --- | --- |
| Example 1 | 0.94 | 1 |
| Example 2 | 1.64 | 2 |

TABLE-continued

|  | Relative Activity | Relative Selectivity |
|---|---|---|
| Example 3 | 1.80 | 2 |
| Comparative Example 1 | 0.66 | <0 |
| Comparative Example 2 | 1.00 | 0 |
| Comparative Example 3 | 1.28 | 0 |
| Comparative Example 4 | 0.95 | 0 |

As can be seen from the data above, control of process variables during the synthesis of a mixed metal oxide catalyst gives improved catalyst performance in activity and selectivity for isobutylene oxidation to methacrolein. In particular, the time of aging or digestion of the reaction slurry with little or no agitation (Examples 1-3) when compared with shorter time of aging or digestion with agitation (Comparative Example 1), longer time of aging or digestion with agitation (Comparative Example 2), or approximately the same time of aging or digestion with agitation (Comparative Examples 3 and 4) addition gives improved catalyst performance in activity and selectivity for isobutylene oxidation to methacrolein. In addition, agitation while forming the reaction slurry (Examples 2 and 3) gives improved catalyst performance in activity and selectivity for isobutylene oxidation to methacrolein when compared with no agitation while forming the reaction slurry (Example 1).

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing catalyst for the oxidation of an olefin to an unsaturated aldehyde comprising:
   a) dissolving compounds of molybdenum, bismuth, iron, cesium, and optional compounds of tungsten, M and M' in water or acid to form a reaction solution,
   wherein M is one or more selected from antimony, phosphorus, boron, sulfur, silicon, aluminum, titanium, tellurium, vanadium, zirconium and niobium and M' is one or more selected from cobalt, nickel, magnesium, zinc, potassium, rubidium, thallium, manganese, barium, chromium, cerium, tin, lead, cadmium and copper;
   b) precipitating a solid in the reaction solution to form a reaction slurry;
   c) aging the slurry for about 5 to about 10 hours with little or no agitation;
   d) evaporating liquid from the slurry to form a solid catalyst precursor;
   e) calcining the solid to form oxides of the metals to form a catalyst of the general formula:

$Mo_{12}Bi_aW_bFe_cCs_gM_mM'_mO_x$ wherein a is in the range from 0.1 to 1.5, b is 0 to 9, c is in the range from 0.2 to 5.0, g is in the range from 0.1 to 1.5, m is in the range from 0 to 9, m' is from 0 to 9 and x is determined by the valences of the other components.

2. The process of claim 1 wherein the molybdenum compound is an ammonium salt.

3. The process of claim 2 wherein the molybdenum compound is ammonium paramolybdate or ammonium molybdate.

4. The process of claim 1 wherein the tungsten compound is an ammonium salt.

5. The process of claim 4 wherein the tungsten compound is ammonium paratungstate or ammonium tungstate.

6. The process of claim 1 wherein the bismuth compound is a nitrate.

7. The process of claim 1 wherein the iron compound is a nitrate.

8. The process of claim 1 wherein M' is a cobalt compound.

9. The process of claim 8 wherein the cobalt compound is a nitrate.

10. The process of claim 1 M' is a nickel compound.

11. The process of claim 10 wherein the nickel compound is a nitrate.

12. The process of claim 1 wherein M is an antimony compound.

13. The process of claim 12 wherein the antimony compound is an oxide.

14. The process of claim 1 wherein the cesium compound is a nitrate.

15. The process of claim 1 wherein M' is a zinc compound.

16. The process of claim 15 wherein the zinc compound is a nitrate.

17. The process of claim 1 wherein M' is a magnesium compound.

18. The process of claim 17 wherein M' is a magnesium nitrate.

19. The process of claim 1 wherein the catalyst is of the formula:

$Mo_{12}Bi_aW_bFe_cCo_dNi_eSb_fCs_gMg_hZn_iO_x$ wherein a is 0.8 to 1.2, b is 0 to 2, c is 2 to 4 d is 0 to 4, e is 3 to 6, f is 0 to 2.0, g is 0.2 to 0.8, h is 0 to 1.5 and i is 0 to 2.0.

20. The process of claim 19 wherein the catalyst is of the formula:

$Mo_{12}Bi_aW_bFe_cCo_dNi_eSb_fCs_gMg_hZn_iO_x$ wherein a is 0.9 to 1.1, b is 0 to 1, c is 2.0 to 2.5, d is 1.0 to 2.0, e is 3.5 to 4.5, f is 0 to 1.0, g is 0.4 to 0.6, h is 0.25 to 0.75 and i is 0 to 1.

21. The process of claim 1 wherein the compounds are dissolved and precipitation occurs at a temperature in the range of from 40° C. to 100° C.

22. The process of claim 21 wherein the compounds are dissolved and precipitation occurs at a temperature in the range of from 60° C. to 95° C.

23. The process of claim 1 wherein aging is for 5 to 6 hours.

24. The process of claim 1 wherein liquid is evaporated at a temperature of 50° to 125° C.

25. The process of claim 1 further comprising drying the catalyst precursor.

26. The process of claim 1 wherein the solid is calcined at a temperature of 200-600° C. for 1-12 hours.

27. The process of claim 1 wherein the solid is calcined in two stages, one at a temperature of 150-400° C. for 1-5 hours and another at a temperature of 460-600° C. for 4-8 hours.

28. The process of claim 27 wherein the two-stage calcination is first at a temperature of 290-310° C. for 2 hours and second at a temperature of 460-500° C. for 6 hours.

29. The process of claim 27 wherein the temperature is increased from the first stage to the second stage at 0.5 to 20° C./min.

30. The process of claim 29 wherein the temperature is increased at 5 to 10° C./min.

31. The process of claim 1 wherein the solid is calcined in one stage at a temperature of 450-500° C. for 1-4 hours.

32. The process of claim 31 wherein the temperature is increased from ambient to the calcination temperature at 0.5 to 20° C./min.

33. The process of claim 32 wherein the temperature is increased at 5 to 10° C./min.

34. The process of claim 1 further comprising agitating the reaction solution.

* * * * *